(12) United States Patent
Tiacci et al.

(10) Patent No.: US 9,222,137 B2
(45) Date of Patent: Dec. 29, 2015

(54) METHOD FOR MONITORING MINIMAL RESIDUAL HAIRY CELL LEUKEMIA

(75) Inventors: Enrico Tiacci, Perugia (IT); Brunangelo Falini, Perugia (IT); Raul Rabadan, New York, NY (US)

(73) Assignee: Trovagene, Inc., San Diego, CA (US)

( * ) Notice: Subject to any disclaimer, the term of this patent is extended or adjusted under 35 U.S.C. 154(b) by 0 days.

(21) Appl. No.: 13/468,283

(22) Filed: May 10, 2012

(65) Prior Publication Data
US 2013/0064789 A1      Mar. 14, 2013

Related U.S. Application Data

(60) Provisional application No. 61/484,330, filed on May 10, 2011.

(51) Int. Cl.
| C12Q 1/68 | (2006.01) |
| A61P 35/02 | (2006.01) |
| A61K 38/21 | (2006.01) |
| A61K 39/00 | (2006.01) |

(52) U.S. Cl.
CPC ........ C12Q 1/6886 (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,797,502 | B2 * | 9/2004 | Kapeller-Libermann | .... 435/198 |
| 6,803,044 | B1 * | 10/2004 | Catania et al. | ............. 424/278.1 |
| 7,598,052 | B2 * | 10/2009 | Giordano et al. | ............ 435/7.23 |
| 7,820,447 | B2 | 10/2010 | Morris et al. | |
| 7,863,288 | B2 * | 1/2011 | Ibrahim et al. | ................ 514/300 |
| 8,110,361 | B2 * | 2/2012 | Laird et al. | ................... 435/6.14 |
| 2007/0020657 | A1 * | 1/2007 | Grebe et al. | ..................... 435/6 |
| 2007/0048754 | A1 * | 3/2007 | Freeman et al. | .................... 435/6 |
| 2010/0173294 | A1 * | 7/2010 | Langland et al. | ................. 435/6 |
| 2011/0158944 | A1 * | 6/2011 | Hosted et al. | ............... 424/85.7 |

OTHER PUBLICATIONS

Jary et al. Real-time allele-specific amplification for sensitive detection of the BRAF mutation V600E, Mol. Cell Probes, 18, 349-352, 2004.*
Pichler et al., Evaluation of high-resolution melting analysis as a diagnostic tool to detect the Braf V600E mutation in colorectal tumors, J. Mol. Diag., 11, 140-147, 2009.*
Pinzani et al., Allele specific Taqman-based real-time PCR assay to quantify circulating BRAFV600E mutated DNA in plasma of melanoma patients. Clin. Chim. Acta. 411, 1319-1324, 2010.*
Ciampi et al., Alterations of the BRAF Gene in thyroid tumors. Endocr. Pathol. 16, 163-172, 2005.*
Wan et al. Mechanism of activation of the RAF-ERK signaling pathway by oncogenic mutations of B-RAF. Cell, 116, 855-867, 2004.*
Shinozaki et al., Utility of circulating B-RAF DNA mutation in serum for monitoring melanoma patients receiving biochemotherapy. Clin. Cancer Res., 13, 2068-2074, 2007.*
Hingorani et al., "Suppression of BRAF(V599E) in human melanoma abrogates transformation", Cancer Res., Sep. 1, 2003, vol. 63, No. 17, pp. 5198-5202.
Gustaffson et al., "Mutations in the BRAF and N-ras genes in childhood acute lymphoblastic leukaemia", Leukemia, Feb. 2005, vol. 19, No. 2, pp. 310-312.
Cocoran et al., "Potential Therapeutic Strategies to Overcome Acquired Resistance to BRAF or MEK Inhibitors in BRAF Mutant Cancers", Oncotarget, Apr. 19, 2011, vol. 2, No. 4, pp. 336-346.
Smith et al., "Mutation of BRAF is uncommon in AML FAB type M1 and M2", Leukemia, Jan. 2003, vol. 17, No. 1, pp. 274-275.
Else et al., "Long-term follow-up of 233 patients with hairy cell leukemia, treated initially with pentostatin or cladribine, at a median of 16 years from diagnosis", Brit. J. Haematol., Jun. 2009, vol. 145, No. 6, pp. 733-740.
Halilovic et al., "Therapeutic strategies for inhibiting oncogenic BRAF signaling", Curr. Opin. Pharmacol., Aug. 2008, vol. 8, No. 4, p. 421, figure 2.
Boyd, E.M. et al., High resolution melting analysis for detection of BRAF exon 15 mutations in hairy cell leukaemia and other lymphoid malignancies, British Journal of Haematology, 2011, 609-612, vol. 155, Issue 5.
Schnittger, S. et al., Minimal residual disease levels assessed by NPM1 mutation-specific RQ-PCR provide important prognostic information in AML, Blood, 2009, 2220-2231. vol. 111, Issue 11.

* cited by examiner

*Primary Examiner* — Elly-Gerald Stoica
(74) *Attorney, Agent, or Firm* — Logue PC; Holly Logue; Elie Gendloff

(57) ABSTRACT

The present invention relates to hairy cell leukemia biomarkers and methods of utilizing these biomarkers to diagnose and/or treat hairy cell leukemia.

11 Claims, 4 Drawing Sheets

METHOD FOR MONITORING MINIMAL RESIDUAL HAIRY CELL LEUKEMIA

CROSS-REFERENCE TO RELATED APPLICATIONS

This application claims the benefit of U.S. Provisional Application No. 61/484,330, filed May 10, 2011, the contents of which are incorporated herein by reference in its entirety.

BACKGROUND OF THE INVENTION

Hairy cell leukemia (HCL) is a hematological malignancy characterized by an accumulation of abnormal B lymphocytes. It is usually classified as a sub-type of chronic lymphoid leukemia. HCL was originally described as histiocytic leukemia, malignant reticulosis, or lymphoid myelofibrosis. The disease was formally named leukemic reticuloendotheliosis and its common name is derived from the "hairy" appearance of the malignant B cells under a microscope.

It is essential to distinguish HCL from other lymphoid malignancies that can masquerade as this disease (e.g., hairy cell variant; splenic marginal zone lymphoma, chronic lymphocytic leukemia, prolymphocytic leukemia, other low grade lymphomas, and systemic mastocytosis). HCL diagnosis is currently based on a combination of methodologies including, physical examination, complete blood count (cbc), peripheral blood smears in conjunction with electron and light microscopy, flow cytometry and tartrate resistant acid phosphatase (TRAP) analysis. However, none of these tests can accurately diagnose HCL and a bone marrow biopsy is required for confirmation.

Accordingly, there is a need in the art to identify genes and proteins which may be dysregulated during the development and progression of hairy cell leukemia, and to utilize these genes and proteins as biomarkers for disease diagnosis and for monitoring disease progression and therapeutic treatment efficacy. The present invention addresses these needs.

SUMMARY OF THE INVENTION

The present invention provides, in part, a method of diagnosing hairy cell leukemia in a subject in need thereof including: obtaining a biological sample from the subject and assessing the presence or absence of a BRAF mutation in the sample, wherein the presence of the BRAF mutation indicates that the subject is suffering from hairy cell leukemia.

The method can further include comparing the presence, absence, or amount of the BRAF mutation in the biological sample with the presence, absence, or amount of the BRAF mutation determined in a biological sample from a subject not suffering from hairy cell leukemia or symptoms thereof. The method can be used to distinguish hairy cell leukemia cells from other forms of malignant lymphoma.

The present invention also provides, in part, a method of treating hairy cell leukemia in a subject in need thereof including: obtaining a biological sample from the subjected, determining the presence or absence of BRAF mutation in the sample and if BRAF mutation is detected in the sample, administering a anti-proliferative agent to the subject, thereby treating the hairy cell leukemia. The method can further include administering a therapeutically effective amount of a BRAF inhibitor or a therapeutically effective amount of a MEK or ERK inhibitor, either alone or in combination with the BRAF inhibitor. The method can further include monitoring minimal residual disease following treatment with a BRAF inhibitor or any anti-leukemic therapy.

The present invention provides, in part, a method for evaluating sensitivity of a hairy leukemic B cell to a BRAF inhibitor including determining if the cells exhibit high expression of a BRAF mutation, when compared to a control, wherein the cells are determined to be sensitive if the high expression is determined. The method can further include administering a therapeutically effective amount of a BRAF inhibitor, alone or in combination with a second anti-proliferative agent, to a mammalian subject containing the hairy leukemic B cells if the cells are determined to be sensitive.

The present invention provides, in part, a method including (a) exposing a subject in need thereof to a candidate compound; (b) obtaining a biological sample from the subject following the exposure; (c) determining the presence, absence, or amount of a BRAF mutation in the biological sample; and, (d) comparing the presence, absence, or amount of the BRAF mutation in the biological sample with the presence, absence, or amount of the BRAF mutation determined in a biological sample obtained from a subject not exposed to the candidate compound. The method can further include identifying a candidate compound capable of reducing or decreasing the BRAF mutation.

The present invention provides, in part, a method including (a) contacting a biological sample with a candidate compound; (b) determining the presence, absence, or amount of a BRAF mutation in the biological sample following contact with the candidate compound; and, (c) comparing the presence, absence, or amount of the BRAF mutation in the biological sample with the presence, absence, or amount of the BRAF mutation determined in a biological sample not contacted with the candidate compound. The method can further include identifying a candidate compound capable of reducing or decreasing the BRAF mutation.

Preferably, the BRAF mutation is a BRAF V600E mutation.

The anti-proliferative agent can be a purine analog, an interferon, rituximab or bendamustine. Preferably, the purine analog is pentostatin, cladaribine, azathioprine, mercaptopurine, thioguanine or fludarabine. Preferably, the BRAF inhibitor is PLX-4032 (Vemurafenib), GSK 2118436 (Dabrafenib), PLX-4720, SB590885. XL-281. RAF-265, GDC-0897 or Sorafenib. Preferably, the MEK or ERK inhibitor is Arry-142886/AZD-6244, SCIO-469, GW681323, U0126, XL-518, CI-1040, PD035901 or GSK1120212.

The present invention provides, in part, a kit for detecting the presence of a BRAF mutation in a biological sample, including a specific binding agent that selectively binds to a BRAF mutation, and instructions for carrying out the method as described herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 2, upper middle panels, show photographs of immunohistochemical analysis of a bone marrow biopsy infiltrated by HCL and stained positively for CD20 and ANXA1. The far right panel shows direct sequencing of purified leukemic cells reveals a homozygous/hemizygous T->A mutation (arrow).

FIG. 2, lower middle panels, show photographs of immunohistochemical analysis of splenic lymphoma/leukemia stained positively for CD20 and negatively for ANXA1. The far right panel shows direct sequencing of purified leukemic cells reveals no T->A mutation (arrow).

FIG. 2, bottom panels, show flow cytometry analysis of splenic marginal zone lymphoma expressing CD19, weakly expressing CD11c but not expressing CD103 or CD25. The far right panel shows direct sequencing of purified leukemic cells reveals no T->A mutation (arrow).

FIG. 3, bottom panels, are photographs showing Western blot analysis of purified HCL cells showing phosphorylation of both MEK and ERK kinases under basal conditions (vehicle treatment) and their dose-dependent dephosphorylation after 2, 6 and 24 h incubation with the specific active BRAF inhibitor PLX-4720 at 250 nM, 500 nM or 1000 nM concentrations.

FIG. 4, right panel, shows staining for phospho-ERK is completely blocked by pre-incubation of the antibody with the specific phospho-ERK peptide.

DETAILED DESCRIPTION OF THE INVENTION

Figure 1:
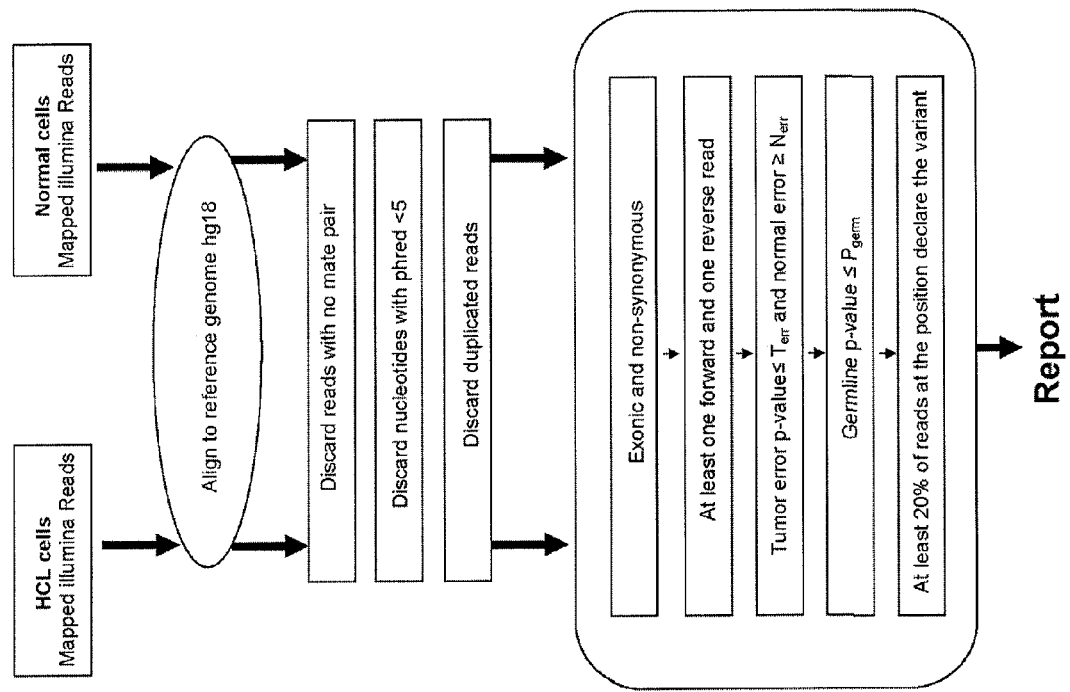
FIG. 1 is a schematic illustrating the bioinformatics pipeline for the identification of somatic mutations.

Hairy cell leukemia (HCL) is a slow growing cancer of the lymphocyte cell line. In the majority of patients, the cell affected is a mature B lymphocyte. The disease begins in the bone marrow but often involves the liver, spleen and sometimes lymph nodes. The symptoms seen in patients with HCL are varied and reflect both direct involvement in organs, secondary effects on the immune system, and release of cytokines or proteins from the malignant cell itself.

The cause of HCL is unknown but risk factors may include exposure to pesticides, herbicides and petrol or diesel fuel. There is no association with cigarette smoking, alcohol or coffee consumption Employment in farming or woodworking is of borderline significance. A familial predisposition has also been suggested due to the clustering of cases within families, but whether this is related to genetic or environmental factors is unknown.

The development of immunologic disorders in association with HCL has been documented in individual case presentations as well as a retrospective review of patients. Patients may present with polyarthritis or diffuse joint pain, erythema nodosum or skin rash, or pulmonary infiltrates. In some cases a diagnosis of lupus or rheumatoid arthritis was entertained before the diagnosis of HCL. Patients can present with systemic symptoms with fever, weight loss, and organ involvement including the liver and kidney. Patients can be treated as necessary with anti-inflammatory drugs including steroids with clinical improvement. Improvement in autoimmune disease does not necessarily respond to effective treatment for the HCL.

The most common complications seen involve the blood and the spleen. The effects on the blood are as follows: The majority of patients will have some degree of reduced blood count with about 40% of patients having depression of all blood cell lines or pancytopenia. In looking at the individual cell lines in large retrospective series anemia as defined by a hemoglobin less than 12 grams/dl is seen in up to 80% of patients with severe anemia with hemoglobin less than 8.5 grams/dl in about one third of patients. This significant anemia may lead to fatigue and reduced exercise tolerance and is often the first symptoms of this disease. The cause of the anemia may be multifactorial including iron deficiency from blood loss and occasionally autoimmune hemolytic anemia. However, the common reason for the anemia is removal of red blood cells in the spleen and marrow infiltration with hairy cells leading to reduced red cell production. Thrombocytopenia is a frequent complication of this disease with platelets less than 100,000/ul in up to 80% of patients. Severe thrombocytopenia of less than 50,000/ul occurs in about one third of patients with about 10% having counts under 20,000/ul. Significant bleeding is usually only seen in severely depressed platelet counts.

The spleen appears to play a significant role, since platelets return to normal after splenectomy in 70% of patients and is especially important in patients with large spleens. However, post splenectomy patients do develop thrombocytopenia due to hairy cell involvement in the marrow and occasionally immune thrombocytopenia is seen.

Leucopenia and neutropenia is one common reason to suspect HCL and leads to one the most severe complications that of significant infections. Life threatening neutropenia with neutrophils of under 500/ul occurs in almost 40% of patients. This depressed white count will often be improved by the use of granulocyte growth factors. An additional diagnostic finding is the presence of marked monocytopenia with resultant susceptibility to unusual organisms.

Hepatomegaly is much less frequent in hairy cell patients with enlargement noted about one third of the time and marked hepatomegaly or greater than 10 cm below the costal margin only 2% of the time. Pain from this hepatomegaly is not common but can occur. The liver is almost always infiltrated with hairy cells without significantly altering hepatic function or elevating liver enzymes. The development of marked hyperbilirubinemia and elevated liver enzyme elevations does occur, but its rarity should make one consider an infectious etiology. In addition, one can see portal hypertension due to involvement with subsequent ascites.

Splenomegaly is one the classic findings found at presentation in patients with hairy cell leukemia. On physical examination up to 90% of patients will have an enlarged spleen and marked splenomegaly of greater than 10 cm below the costal margin seen in 20% of patients. The enlarged spleen may cause early satiety with subsequent weight loss and can be associated with painful splenic infarction or splenic rupture.

One of the most recognized and important, clinical problem in patients with HCL is the development of severe life threatening and unusual infections. These may involve the common sites of lung and urinary tract as well as less common involvement of the liver and central nervous system. Patients may develop a wide range of infections including those usually seen in the neutropenic host such as *Staphylococcus aureus*. *Pseudomonas aeruginosa* Herpes zoster with painful skin lesions is usually only seen after patients have been treated with chemotherapy. Patients with fever of unknown origin should always be treated as if they have a significant infection and a careful search for bacterial, fungal, or viral infection be initiated.

Several other unusual complications can be seen. Neurologic complications including symptoms and signs of meningitis and nerve compression has been reported but one should always look for infection as a cause. Lymphadenopathy is infrequent and when it is present usually involves the chest or abdominal nodes. These can be bulky and cause symptoms of compression. Destructive bone lesions with severe pain can be seen usually in long bones or vertebrae. Finally, involvement of the lining of the lung cavity or pleura or that of the abdominal cavity or peritoneal surface can lead to accumulation of fluid in these areas with symptoms of abdominal pain and or shortness of breath.

Accurate diagnosis of HCL is important since very effective therapy used for treatment of HCL is much less effective in other types of chronic B cell lymphoproliferative disorders. Diagnosis is currently established based on a combination of morphologic and immunophenotypic findings. Blood smear, bone marrow aspirate smears, bone marrow touch preparations and bone marrow biopsy are most often used for diagnosis of HCL. If available; spleen, liver biopsy or rarely other tissue involved by HCL may be used for diagnosis of HCL as well.

There is no cure for hairy cell leukemia. However, some current treatments are effective at putting hairy cell leukemia in remission for years. Currently, treatment of HCL is based upon highly effective purine nucleoside analogs (Greyer M R. Blood; 115(1):21-8). The two purine analog chemotherapy drugs used predominantly for the treatment of HCL are cladaribine (Leustatin) and pentostatin (Nipent). Cladribine is administered as a continuous intravenous infusion over seven days. Side effects of cladribine treatment include infection and fever. Pentostatin is administered by intravenous infusion every other week, for three to six months. Side effects of pentostatin treatment include fever, infection and kidney problems.

In addition to chemotherapy, biological therapies, such as immunotherapy can be utilized. Two types of biological treatments are used predominantly for the treatment of HCL: interferon and rituximab (rituxan). Interferon is often administered when chemotherapy is deemed ineffective. Interferon is usually administered for the period of a year. Side effects include flu-like symptoms, such as fever and fatigue. Rituximab is a monoclonal antibody, normally utilized to treat non-Hodgkin's lymphoma. I Side effects of rituximab include fever and infection.

Other treatments such as splenectomy, bone marrow transplants, blood transfusions or filgrastm therapy may also be employed.

With appropriate treatment, the overall projected lifespan for patients is normal or near-normal. In all patients, the first two years after diagnosis have the highest risk for fatal outcome; generally, surviving five years predicts good control of the disease.

In spite of the remarkable progress in the diagnosis and treatment of HCL over the past 50 years, its underlying genetic alterations remain obscure (Tiacci et al., Nat Rev Cancer 2006; 6(6):437-48). Major obstacles to molecular characterization of HCL have been the scarcity of tumor cells available for analysis (due to frequent pancytopenia), the very low proliferative index of leukemic cells, the inability to grow them in immunodeficient mice and the absence of human cell lines of authentic HCL origin.

No recurrent chromosomal translocations have been identified in HCL (Foucar, et al., WHO Classification of Tumours of Haematopoietic and Lymphoid Tissues. 4th ed. Lyon: International Agency for Research on Cancer (IARC); 2008: 188-90). Gene expression profiling studies revealed a unique molecular signature that in part justifies the distinctive features of HCL cells, like their morphological appearance, adhesion properties, selective homing to extranodal sites and marrow fibrosis (Basso, et al. J Exp Med 2004; 199(1):59-68). However, these studies did not pinpoint any recurrent genetic alteration. Similarly, high density genome-wide SNP genotyping showed a remarkably balanced genomic profile in HCL (Forconi, et al. Br J Haematol 2008; 141(5):622-30).

The present invention provides a highly specific HCL biomarker and methods of utilizing this biomarker for detecting HCL. The present invention utilized in-solution exome capture followed by massively parallel sequencing to identify novel acquired alterations (Campbell, et al. Nat Genet. 2008; 40(6):722-9; Ley, et al. Nature 2008; 456(7218):66-72) in the DNA of purified peripheral blood (PB) leukemic and paired normal mononuclear cells from HCL patients.

Specifically, the present invention identified the BRAF V600E mutation as a genetic alteration recurrently associated with HCL. The BRAF V600E mutation qualifies as a disease-defining genetic event in HCL because of: i) its presence in 100% of cases encompassing the whole spectrum of HCL patients, including those presenting with leukocytosis or without splenomegaly and those analyzed after therapy; ii) its presence in the entire tumor cell clone in virtually all patients; and iii) its restriction to HCL among peripheral B-cell lymphomas/leukemias. This demonstrates the BRAF V600E mutation in HCL pathogenesis. Notably, among B-cell neoplasms (in which non-kinase genes are usually involved by a variety of genetic alterations, i.e. translocations, deletions, or point mutations), HCL is the only one whose disease-defining genetic lesion is represented by an activating point mutation of a kinase-encoding gene. Surprisingly, the frequency of BRAF V600E in HCL far outnumbers that previously reported for other BRAF-mutated human neoplasms, including melanomas (~50%) (Davies, et al. Nature 2002; 417 (6892):949-54; urtin, et al. N Engl J Med 2005; 353(20): 2135-47), papillary thyroid carcinomas (~40%) (Puxeddu, et al. J Clin Endocrinol Metab 2004; 89(5):2414-20), Langherans cell histiocytosis (57%) (Badalian-Very, et al. Blood; 116(11):1919-23) and a variety of solid tumors (at much lower frequency)(Davies, et al. Nature 2002; 417(6892):949-54; Brose, et al. Cancer Res 2002; 62(23):6997-7000; Tie, et al. Int J Cancer 2011 May 1; 128(9):2075-84).

Preferably, the BRAF mutation is a BRAF V600E mutation, in which a glutamic acid (Glu or E) is substituted for a Valine (Val or V) residue at position or amino acid residue 600 of SEQ ID NO: 2. Alternatively, or in addition, the BRAF mutation is a substitution of an adenine (A) for a thymine (T) nucleotide at position 1860 of SEQ ID NO: 1.

*Homo sapiens* v-raf murine sarcoma viral oncogene homolog B1, BRAF, is encoded by the following mRNA sequence (NM_004333, SEQ ID NO: 1) (coding sequence is bolded and the coding sequence for amino acid residue 600 is underlined):

```
   1 cgcctccctt cccctcccc gcccgacagc ggccgctcgg gccccggctc tcggttataa
  61 gatggcggcg ctgagcggtg gcggtggtgg cggcgcggag ccgggccagg ctctgttcaa
 121 cggggacatg gagcccgagg ccggcgccgg cgccggcgcc gcggcctctt cggctgcgga
 181 ccctgccatt ccggaggagg tgtgaatat caaacaaatg attaagttga cacaggaaca
 241 tatagaggcc ctattggaca aatttggtgg ggagcataat ccaccatcaa tatatctgga
 301 ggcctatgaa gaatacacca gcaagctaga tgcactccaa caaagagaac aacagttatt
 361 ggaatctctg gggaacggaa ctgattttc tgtttctagc tctgcatcaa tggataccgt
 421 tacatcttct tcctcttcta gcctttcagt gctaccttca tctctttcag tttttcaaaa
 481 tcccacagat gtggcacgga gcaaccccaa gtcaccacaa aaacctatcg ttagagtctt
 541 cctgcccaac aaacagagga cagtggtacc tgcaaggtgt ggagttacag tccgagacag
 601 tctaaagaaa gcactgatga tgagaggtct aatcccagag tgctgtgctg tttacagaat
 661 tcaggatgga gagaagaaac caattggttg gacactgat atttcctggc ttactggaga
 721 agaattgcat gtggaagtgt tggagaatgt tccacttaca acacacaact tgtacgaaa
 781 aacgttttc accttagcat tttgtgactt ttgtcgaaag ctgcttttcc agggtttccg
 841 ctgtcaaaca tgtggttata aatttcacca gcgttgtagt acagaagttc cactgatgtg
 901 tgttaattat gaccaacttg atttgctgtt tgtctccaag ttctttgaac accacccaat
 961 accacaggaa gaggcgtcct tagcagagac tgccctaaca tctggatcat ccccttccgc
1021 acccgcctcg gactctattg ggccccaaat tctcaccagt ccgtctcctt caaaatccat
1081 tccaattcca cagcccttcc gaccagcaga tgaagatcat cgaaatcaat ttgggcaacg
1141 agaccgatcc tcatcagctc ccaatgtgca tataaacaca atagaacctg tcaatattga
1201 tgacttgatt agagaccaag gatttcgtgg tgatggagga tcaaccacag gtttgtctgc
1261 tacccccct gcctcattac ctggctcact aactaacgtg aaagccttac agaaatctcc
1321 aggacctcag cgagaaagga agtcatcttc atcctcagaa gacaggaatc gaatgaaaac
1381 acttggtaga cgggactcga gtgatgattg ggagattcct gatgggcaga ttacagtggg
1441 acaaagaatt ggatctggat catttggaac agtctacaag ggaaagtggc atggtgatgt
1501 ggcagtgaaa atgttgaatg tgacagcacc tacacctcag cagttacaag ccttcaaaaa
1561 tgaagtagga gtactcagga aaacacgaca tgtgaatatc ctactcttca tgggctattc
1621 cacaaagcca caactggcta ttgttaccca gtggtgtgag ggctccagct tgtatcacca
1681 tctccatatc attgagacca aatttgagat gatcaaactt atagatattg cacgacagac
1741 tgcacagggc atggattact tacacgccaa gtcaatcatc cacagagacc tcaagagtaa
1801 taatatattt cttcatgaag acctcacagt aaaaataggt gattttggtc tagctacagt
1861 gaaatctcga tggagtgggt cccatcagtt tgaacagttg tctggatcca ttttgtggat
1921 ggcaccagaa gtcatcagaa tgcaagataa aaatccatac agctttcagt cagatgtata
1981 tgcatttgga attgttctgt atgaattgat gactggacag ttaccttatt caaacatcaa
2041 caacagggac cagataattt ttatggtggg acgaggatac ctgtctccag atctcagtaa
2101 ggtacggagt aactgtccaa aagccatgaa gagattaatg gcagagtgcc tcaaaaagaa
2161 aagagatgag agaccactct ttccccaaat tctcgcctct attgagctgc tggcccgctc
2221 attgccaaaa attcaccgca gtgcatcaga accctccttg aatcgggctg gtttccaaac
2281 agaggatttt agtctatatg cttgtgcttc tccaaaaaca cccatccagg caggggata
2341 tggtgcgttt cctgtccact gaaacaaatg agtgagagag ttcaggagag tagcaacaaa
2401 aggaaaataa atgaacatat gtttgcttat atgttaaatt gaataaaata ctctcttttt
```

-continued

```
2461 ttttaaggtg aaccaaagaa cacttgtgtg gttaaagact agatataatt tttccccaaa 2521 ctaaaattta tacttaacat tggattttta acatccaagg gttaaaatac atagacattg 2581 ctaaaaattg gcagagcctc ttctagaggc tttactttct gttccgggtt tgtatcattc 2641 acttggttat tttaagtagt aaacttcagt ttctcatgca acttttgttg ccagctatca 2701 catgtccact agggactcca gaagaagacc ctacctatgc ctgtgtttgc aggtgagaag 2761 ttggcagtcg gttagcctgg gttagataag gcaaactgaa cagatctaat ttaggaagtc 2821 agtagaattt aataattcta ttattattct taataatttt tctataacta tttcttttta 2881 taacaatttg gaaaatgtgg atgtctttta tttccttgaa gcaataaact aagtttcttt 2941 ttataaaaa
```

*Homo sapiens* v-raf murine sarcoma viral oncogene homolog B1, BRAF, is encoded by the following amino acid sequence (NP_004324, SEQ ID NO: 2) (amino acid residue 600 is bolded and underlined):

```
  1 maalsggggg gaepgqalfn gdmepeagag agaaassaad paipeevwni kqmikltqeh 61 iealldkfgg ehnppsiyle ayeeytskld alqqreqqll eslgngtdfs vsssasmdtv 121 tsssssslsv lpsslsvfqn ptdvarsnpk spqkpivrvf lpnkqrtvvp arcgvtvrds 181 lkkalmmrgl ipeccavyri qdgekkpigw dtdiswltge elhvevlenv pltthnfvrk 241 tfftlafcdf crkllfqgfr cqtcgykfhq rcstevplmc vnydqldllf vskffehhpi 301 pqeeaslaet altsgsspsa pasdsigpqi ltspspsksi pipqpfrpad edhrnqfgqr 361 drsssapnvh intiepvnid dlirdqgfrg dggsttglsa tppaslpgsl tnvkalqksp 421 gpqrerksss ssedrnrmkt lgrrdssddw eipdgqitvg qrigsgsfgt vykgkwhgdv 481 avkmlnvtap tpqqlqafkn evgvlrktrh vnillfmgys tkpqlaivtq wcegsslyhh 541 lhiietkfem iklidiarqt aqgmdylhak siihrdlksn niflhedltv kigdfglat*v*

601 ksrwsgshqf eqlsgsilwm apevirmqdk npysfqsdvy afgivlyelm tgqlpysnin 661 nrdqiifmvg rgylspdlsk vrsncpkamk rlmaeclkkk rderplfpqi lasiellars 721 lpkihrsase pslnragfqt edfslyacas pktpiqaggy gafpvh
```

A member of the serine/threonine kinase RAF family, the BRAF protein is part of the RAS-RAF-MAPK signaling pathway that plays a major role in regulating cell survival, proliferation and differentiation (Keshet and Seger. Methods Mol Biol; 661:3-38). BRAF mutations constitutively activate the MEK-ERK pathway, leading to enhanced cell proliferation, survival and ultimately, neoplastic transformation (Wellbrock and Hurlstone. Biochem Pharmacol; 80(5):561-7; Li et al. Oncol Rep 2009; 22(4):671-81; Niault and Baccarini. Carcinogenesis; 31(7):1165-74). All BRAF mutated HCL cases carried the V600E phospho-mimetic substitution which occurs within the BRAF activation segment and markedly enhances its kinase activity in a constitutive manner (Wan, et al. Cell 2004; 116(6):855-67).

The BRAF V600E mutation accounts for some HCL immunophenotypic features, e.g. the low/moderate cyclin D1 expression (which is independent of CCND1 rearrangements or amplifications) (Bosch, et al. Br J Haematol 1995; 91(4):1025-30; Miranda, et al. Mod Pathol 2000; 13(12):1308-14) and absence of p27 (Chilosi, et al. Br J Haematol 2000; 111(1):263-71). In melanoma cells, V600E BRAF leads to MEK/ERK pathway activation with concomitant transcriptional constitutive expression of cyclin D1 and p27 down-regulation in an adhesion-independent manner (Roovers, et al. Mol Biol Cell 1999; 10(10):3197-204; Bhatt et al. Oncogene 2005; 24(21):3459-71; Bhatt et al. Oncogene 2007; 26(7):1056-66). Moreover, MEK-ERK-induced activation of an AP1-transcription factor complex containing JUND (Nicolaou, et al. Blood 2003; 101(10):4033-41) has been implicated in the expression of the HCL marker CD11c.

BRAF V600E was present in all 47 HCL cases analyzed. Among a total of 240 peripheral B-cell lymphomas studied, BRAF V600E was restricted to HCL.

The present invention demonstrates that BRAF mutations, such as BRAF V600E, can be readily utilized as a diagnostic biomarker to distinguish HCL from other B-cell lymphomas exhibiting similar clinical and morphological features, such as HCL-variant and splenic marginal zone lymphoma, none of which were positive for BRAF-mutations. This distinction is critically relevant clinically since HCL but not HCL-like disorders respond optimally to interferon or purine analogs (Greyer M R. Blood; 115(1):21-8). Absence of BRAF mutations in HCL-variant further supports the view that this entity is different from HCL and justifies its inclusion in the category of splenic B-cell lymphoma/leukemia, unclassifiable in the 2008 WHO classification (Piris et al. WHO classification of tumours of haematopoietic and lymphoid tissues. 4th edition ed. Lyon: International Agency for Research on Cancer (IARC); 2008).

Additionally, the present invention demonstrates that BRAF mutations, such as the BRAF V600E mutation, are therapeutic targets for HCL patients who do not respond or respond suboptimally to initial therapy with purine analogs as well as for patients experiencing repeated relapses or unacceptable toxicities or to be utilized in combination with purine analog treatment (Greyer M R. Blood; 115(1):21-8). Notably, BRAF V600E inhibitors (Tsai, et al. Proc Natl Acad Sci USA 2008; 105(8):3041-6; Sala, et al. Mol Cancer Res 2008; 6(5):751-9; Bollag, et al. Nature; 467(7315):596-9) have shown remarkable activity in patients with BRAF-mutated metastatic melanoma (Flaherty, et al. The New England Journal of Medicine 2010; 363:809-19). The present invention also provides a treatment regimen where active BRAF inhibitors can be utilized in combination with compounds acting downstream of BRAF (e.g., MEK or ERK inhibitors), in HCL patients.

The present invention provides, in part, a method of diagnosing hairy cell leukemia in a subject in need thereof including: obtaining a biological sample from the subject and assessing the presence or absence of a BRAF mutation in the sample, wherein the presence of the BRAF mutation indicates that the subject is suffering from hairy cell leukemia.

The method can further include comparing the presence, absence, or amount of the BRAF mutation in the biological sample with the presence, absence, or amount of the BRAF mutation determined in a biological sample from a subject not suffering from hairy cell leukemia or symptoms thereof. The method can be used to distinguish hairy cell leukemia cells from other forms of malignant lymphoma.

The present invention also provides, in part, a method of treating hairy cell leukemia in a subject in need thereof including: obtaining a biological sample from the subjected, determining the presence or absence of BRAF mutation in the sample and if BRAF mutation is detected in the sample, administering a anti-proliferative agent to the subject, thereby treating the hairy cell leukemia. The method can further include administering a therapeutically effective amount of a BRAF inhibitor or a therapeutically effective amount of a MEK or ERK inhibitor, either alone or in combination with the BRAF inhibitor.

The present invention also includes a method of monitoring minimal residual disease following treatment an anti-proliferative (i.e., anti-leukemic) agent. The method includes obtaining a biological sample from the subjected following treatment, determining the presence or absence of BRAF mutation in the sample and if BRAF mutation is detected in the sample, administering additional anti-proliferative agents to the subject. As used herein, minimal residual disease (MRD) refers to the leukemia cells (HCL cells) that remain in the patient during treatment or after treatment when the patient is in remission (no symptoms or signs of disease). MRD is the major cause of relapse in cancer and leukemia (HCL). Monitoring MRD has several important roles: determining whether treatment has eradicated the cancer or whether traces remain, comparing the efficacy of different treatments, monitoring patient remission status and recurrence of the leukemia or cancer and choosing the treatment that will best meet those needs (personalization of treatment).

The present invention provides, in part, a method for evaluating sensitivity of a hairy leukemic B cell to a BRAF inhibitor including determining if the cells exhibit high expression of a BRAF mutation, when compared to a control, wherein the cells are determined to be sensitive if the high expression is determined. The control can be a normal B cell. The control can be the average expression of a BRAF mutation in a population of hairy leukemic B cells, wherein high expression means higher than the average of the population. The method can further include administering a therapeutically effective amount of a BRAF inhibitor, alone or in combination with a second anti-proliferative agent, to a mammalian subject containing the hairy leukemic B cells if the cells are determined to be sensitive.

The present invention provides, in part, a method including (a) exposing a subject in need thereof to a candidate compound; (b) obtaining a biological sample from the subject following the exposure; (c) determining the presence, absence, or amount of a BRAF mutation in the biological sample; and, (d) comparing the presence, absence, or amount of the BRAF mutation in the biological sample with the presence, absence, or amount of the BRAF mutation determined in a biological sample obtained from a subject not exposed to the candidate compound. The method can further include identifying a candidate compound capable of reducing or decreasing the BRAF mutation.

The present invention provides, in part, a method including (a) contacting a biological sample with a candidate compound; (b) determining the presence, absence, or amount of a BRAF mutation in the biological sample following contact with the candidate compound; and, (c) comparing the presence, absence, or amount of the BRAF mutation in the biological sample with the presence, absence, or amount of the BRAF mutation determined in a biological sample not contacted with the candidate compound. The method can further include identifying a candidate compound capable of reducing or decreasing the BRAF mutation.

Preferably, the BRAF mutation is a BRAF V600E mutation.

The anti-proliferative agent can be a purine analog, an interferon, rituximab or bendamustine. Preferably, the purine analog is pentostatin, cladaribine, azathioprine, mercaptopurine, thioguanine or fludarabine. Preferably, the BRAF inhibitor is PLX-4032 (Vemurafenib), GSK 2118436 (Dabrafenib), PLX-4720, SB590885. XL-281. RAF-265, GDC-0897 or Sorafenib. Preferably, the MEK or ERK inhibitor is Arry-142886/AZD-6244, SC10-469, GW681323, U0126, XL-518, CI-1040, PD035901 or GSK1120212.

The present invention also provides, in part, a kit for detecting the presence of a BRAF mutation in a biological sample, including a specific binding agent that selectively binds to a BRAF mutation, and instructions for carrying out the method as described herein.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, a "subject in need thereof" is a subject having a cell proliferative disorder, or a subject having an increased risk of developing a cell proliferative disorder relative to the population at large. Preferably, a subject in need thereof has cancer. More preferably, a subject in need thereof has hairy cell leukemia or shows symptoms of suffering from hairy cell leukemia. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be administered in amount sufficient to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin, some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a chemotherapeutic agent. The chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor, a HER2 inhibitor, a histone deacetylase inhibitor, a hormone; a mitotic inhibitor, an MTOR inhibitor, a multi-kinase inhibitor, a serine/threonine kinase inhibitor; a tyrosine kinase inhibitors; a VEGF/VEGIR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine$^{131}$ tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iress a); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WH1-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limitedto, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WH1-P154 (targets JAK), WH1-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCID-469 (targets MAP/MEK), GW681323 (targets MAP/MEK), CC-401 (targets INK), CEP-1347 (targets JNK), and PD 332991 (targets CDK).

The present invention also provides pharmaceutical compositions comprising a candidate compound of the present invention in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use.

A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze drying that yields a powder of the active ingredient plus any additional desired ingredient from a previously sterile filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day.

In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in pro-drug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., Design of Prodrugs, p1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19<sup>th</sup> edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Methods

The following methods described herein were utilized in the examples that follow.

Biological Samples:

Criteria for HCL diagnosis were according to the WHO 2008 classification (Foucar, et al., WHO Classification of Tumours of Haematopoietic and Lymphoid Tissues. 4th ed. Lyon: International Agency for Research on Cancer (IARC); 2008:188-90). All 47 cases showed the typical clinical picture and morphology of HCL, were positive for Annexin A1 (Falini, et al. Lancet 2004; 363(9424):1869-70) on immunohistochemistry and/or co-expressed CD11c, CD25 and CD103 at flow cytometry.

Whole exome sequencing in the index HCL patient was performed on purified (>90%) CD19-positive leukemic cells at disease onset and purified (>98%) CD19-negative PB mononuclear cells after chemotherapy, as described in detail herein.

Whole Exome Sequencing and Bioinformatic Analyses:

Preparation of shotgun libraries from the leukemic and non-leukemic genomic DNA of the index patient, followed by in-solution exome capture, was performed using a commercial platform (Agilent) covering 38 Mb of coding exons (~1.22% of the genome). After massively parallel sequencing with the Illumina Genome Analyzer IIx, candidate somatic mutations were identified according to a bioinformatic pipeline (FIG. 1). Specifically, after aligning the Illumina reads from the HCL and the normal cell DNA to the human reference genome, a series of filters were applied to discard reads not usable for the downstream purpose of somatic mutation discovery. Sequence variants fulfilling the further 5 criteria indicated in the bottom rectangle were subjected to Sanger sequencing validation.

Validation and screening of candidate mutations by PCR amplification and Sanger sequencing:

Candidate non-synonymous somatic variants (present in the tumor but not in its paired normal DNA) were verified by PCR amplification and direct DNA sequencing of the same patient samples subjected to whole exome sequencing. Because the sensitivity of Sanger sequencing permits detection of heterozygous mutations only when present in a major clonal population, sequence variants reported in <25% of the reads were not included in this validation phase.

PCR and direct DNA Sanger sequencing of BRAF exon15 in an extended cohort of HCL patients (n=46) or other peripheral B-cell lymphomas/leukemias (n=193) were performed using the primers e15F-5'-TACCTAAACTCTTCATAAT-GCTTGC-3' (SEQ ID NO: 3) and e15R5'-GTAACTCAG-CAGCATCTCAGGG-3' (SEQ ID NO: 4). Cycling conditions (after the initial denaturation step at 94° C. for 2') were 94° C. for 30", 56° C. for 3 0", 72° C. for 20" for 40 cycles, followed by a final elongation at 72° C. for 10'. For 48 diffuse large B-cell lymphomas (DLBCLs) primers and cycling conditions are reported in Tables S1 and S2.

TABLE S1

| Gene | Exon | CCDS # | Oligonucleotide Name | Oligonucleotide Sequence |
|---|---|---|---|---|
| BRAF | 15 | CCDS5863.1 | BRAF-E15F | TTTGTGAATACTGGGAACTATGAAA (SEQ ID NO: 5) |
| | | | BRAF-E15R | TCATCCTAACACATTTCAAGCC (SEQ ID NO: 6) |
| CNTN6 | 11 | CCDS2557.1 | CNTN6-E11F | TTAATATGCTTTGAAATCGACAATG (SEQ ID NO: 7) |
| | | | CNTN6-E11R | CAGGTTTGACACCATAACACAAG (SEQ ID NO: 8) |
| CSMD3 | 65 | CCDS6315.1 | CSMD3-E65F | AGCCAACAAATTTCCCTTGTT (SEQ ID NO: 9) |
| | | | CSMD3-E65R | CCACAAATGGTGGATTAGGAA (SEQ ID NO: 10) |
| OR8J1 | 1 | CCDS31529.1 | OR8J1-E1F | AACCTCTCTTTTCCCCCAAA (SEQ ID NO: 11) |
| | | | OR8J1-E1R | AGCCACATAGCGGTCATAGG (SEQ ID NO: 12) |
| SLC5A1 | 6 | CCDS13902.1 | SLC5A1-E6F | GTTGTGTGGCAAAGAAACTGC (SEQ ID NO: 13) |
| | | | SLC5A1-E6R | TCCTCAAGAAGAGAAACCACCTC (SEQ ID NO: 14) |

TABLE S2

| | Gene name | | | | |
|---|---|---|---|---|---|
| | BRAF | CNTN6 | CSMD3 | OR8J1 | SLC5A1 |
| Primers | BRAF-E15F/R | CNTN6-E11F/R | CSMD3-E65F/R | OR8J1-E1F/R | SLC5A1-E6F/R |
| Genomic DNA | 20 ng | 20 ng | 20 ng | 20 ng | 20 ng |
| Buffer 10X | 2.5 ul | — | 2.5 ul | — | — |
| MgCl2 | 2.5mM final | — | 2.5mM final | — | — |
| Buffer3 (Roche) | — | 2.5 ul | — | 2.5 ul | 2.5 ul |
| dNTP 10 mM | 0.5 ul | 0.5 ul | 0.5 ul | 0.5 ul | 0.5 ul |
| 5' primer (10 pM/mL) | 0.5 ul | 0.5 ul | 0.5 ul | 0.5 ul | 0.5 ul |
| 3' primer (10 pM/mL) | 0.5 ul | 0.5 ul | 0.5 ul | 0.5 ul | 0.5 ul |
| TAQ Polymerase | 0.3 ul | 0.3 ul | 0.3 ul | 0.3 ul | 0.3 ul |
| DMSO | — | 5% | — | 5% | 5% |
| 10x Enhancer Solution | 1X | — | — | — | — |
| ddH2O | up to 25 uL | up to 25 uL | up to 25 uL | up to 25 uL | up to 25 uL |
| N of cycles | 35 | TD PCR* | 35 | TD PCR* | TD PCR* |
| Annealing Temperature | 56 C. | | 62 C. | | |
| Extension time | 1' | | 1' | | |

All 239 patient samples investigated had ≥30% neoplastic cells.

Patient Samples and Purification of HCL Cells:

For whole exome sequencing (WES) of the index HCL patient, leukemic cells were purified from peripheral blood (PB) at disease onset using Ficoll density gradient centrifugation and subsequent MACS (Magnetic-Activated Cell Sorting) of mononuclear cells with CD19-Microbeads and LS columns (Miltenyi Biotech). Purity of leukemic cells was >90%, as assessed by morphological and immunophenotypic analysis of the eluted cells on cytospins stained with the May-Grunwald-Giemsa solution and with an anti-CD20 monoclonal antibody, respectively. Non-leukemic cells were isolated from the same patient after chemotherapy by negative selection with CD19-microbeads on LD columns (Miltenyi Biotech). Flow cytometry analysis of the CD19-negative (i.e., non-leukemic) cell fraction documented a purity of >98%.

For DNA Sanger sequencing of the extended cohort of HCL patients (n=39), leukemic cells were enriched in 38 of them from peripheral blood using Ficoll density gradient centrifugation, followed in 25 patients by further enrichment with CD19-MACS positive selection. In 9 patients, the post-Ficoll pellet was subjected to red blood cell lysis to obtain granulocytes as a source of germline DNA. The proportions of leukemic and non-leukemic cells in all of these 38 and 9 samples, respectively, was assessed by flow cytometry analysis for co-expression of CD19 with CD11c (and/or CD103c) and for lack of CD19 expression, respectively, and ranged from 30% to >90% for the leukemic cells and was always >90% for the non-leukemic cells. In a single HCL patient, the source of leukemic cell material was represented by frozen sections of a splenectomy specimen with >80% tumor infiltration; granulocytes (>90% pure) were obtained from the PB of this patient as well, as described herein.

For DNA Sanger sequencing of the patients with B-cell neoplasms other than HCL (n=192) neoplastic cells were represented either by the post-Ficoll mononuclear cell fraction of peripheral blood samples, bone marrow aspirates and splenectomy-derived cell suspensions (in the case of splenic marginal zone lymphoma, splenic lymphoma/leukemia unclassifiable, chronic lymphocytic leukemia and some Burkitt lymphomas), or from frozen sections of involved tissues (in the case of diffuse large B-cell lymphoma, mantle cell lymphoma, follicular lymphoma and the rest of Burkitt lymphomas). The proportion of neoplastic B cells was ≥30% in all such cases.

Extraction of high molecular weight genomic DNA from normal and pathological samples was performed using the Gentra Puregene kit (Qiagen) or standard phenol/chloroform extraction following proteinase K digestion.

In-solution exome capture and massively parallel sequencing of the HCL patient:

Preparation of ~250 base pair long genomic shotgun libraries from the leukemic and non-leukemic patient DNA, followed by in-solution exome capture, was performed using the commercial Agilent platform, in particular the Paired-End Sequencing Library Prep for Illumina (version 1.0.1) and the SureSelect Human All Exon Kit (version 1.0, covering 38 Mb of coding exons, which represent ~1.22% of the genome). PCR cycles for pre-capture and post-capture library amplification were 10 and 14, respectively. As quality controls for the pre-capture and post-capture steps, clones of the PCR products were Sanger-sequenced to verify their preferential alignment to human genomic regions (pre-capture) and to human coding transcripts (post-capture). Sequencing was performed on the Illumina Genome Analyzer GAIIx for 2×108 cycles using Chrysalis sequencing kit version 4.0. The base-calling was performed with GAPipeline version 1.5.1 and produced ~22.4 millions pass filter sequences of 2×108 bases per channel/library, which represents 4.8 Gb per channel/library. Mapping on the human genome assembly hg18/NCBI36.1 was performed using the MAQ software version 0.7.1, accepting up to 2 mismatches in the first 24 bases (seed) and considering a maximum insert size of 600 bp. Approximately 66% of all mapped reads actually mapped to an exon target +/−100 bases, documenting the successful technical outcome of this whole exome sequencing experiment.

Bioinformatics approach for the identification of candidate somatic variants:

Low-quality reads (average Phred score <5) and duplicate reads (defined as reads mapping to the exact same position on the genome) were removed. Since the genomic library was sequenced from both ends, thus generating paired-end reads, a different filter was also tested in which two inserts were considered duplicates (and therefore removed) if both their paired-end reads started at the same position. Independent of the method used, the fraction of duplicate reads corresponded to 5-10%, Sequence variants, i.e. different from the reference human genome sequence (hg18 assembly), were identified in each sample separately, and the following were removed: synonymous variants, variants present in the paired normal DNA, and variants likely representing sequencing errors, as assessed by the SAVI algorithm (Statistical Algorithm for Variant Identification) developed at Columbia University.

The algorithm takes into account the depth of a variant and the total depth at a particular position from both the tumor and normal sample, allowing small contaminations of tumor cells in the normal sample and vice versa. Three p-values are calculated, which involve an estimate of the mean error rate of sequencing (~1%), and measure the significance of the hypothesis that: i) the tumor variant is not an error (Terr p-value); the presence of the variant in normal is due to an error (Nerr p-value); and iii) the variant present in the tumor is not somatic, i.e. is germline (germline p-value). Assuming that variants appearing in the normal but not in the tumor sample are false positives, an estimate of the false discovery rate (FDR) was obtained for every possible pair of cut-offs for the error and germline p-values by contrasting the number of identified variants in the normal versus tumor comparison to that in the tumor versus normal comparison. To minimize the FDR, a cut-off of $10^{-6}$ was then chosen for both the error p-values and the germline p-value. Moreover, candidate variants were filtered out if not present in at least one read from each strand (i.e., ≥1 read on the forward strand and ≥1 read on the reverse strand, abbreviated as Fwd≥1, Rev≥1), because it was observed that variants identified in only one strand are mostly due to sequencing errors (not shown). Finally, variants were excluded from the validation phase if present in less than 25% of the reads, based on previous observations documenting the inability of Sanger sequencing to detect mutations represented in such a low proportion of alleles (not shown).

The sensitivity of the approach, defined as the total number of true variants identified, was estimated based on the total number of known (i.e., present in dbSNP130) germline polymorphisms detected by the approach using an error p-value cut-off of at most 1e-6 and the criterion Fwd≥1 and Rev≥1. This calculation produced 13,385 known SNPs and 2,720 new variants in the tumor (Table S5), in keeping with other estimates from previous studies (Choi, et al. Proc Natl Acad Sci USA 2009; 106(45):19096-101; Ng, et al. PLoS Genet. 2008; 4(8):e1000160).

TABLE S5

| Tumor variants affecting CDS and splice sites | Fwd > 0 Rev > 0 Terr < = $10^{-6}$ Germ < = $10^{-6}$ % > = 25 | | | | Validated by Sanger sequencing |
|---|---|---|---|---|---|
| 5748811 | 161189 | 379 | 20 | 5 | 5 |

In table S5, the first column shows the number of variants affecting coding sequences (CDS) and splice sites, which were not reported as common SNPs. Columns 2-5 indicate the number of variants obtained after each of the additional filtering steps including: presence in at least one forward and one reverse strand read ($2^{nd}$ column), error p-value in the tumor sample <=$10^{-6}$ ($3^{rd}$ column), germline p-value <=$10^{-6}$ ($4^{th}$ column), variant frequency >=25% ($5^{th}$ column). The last column indicates the number of candidate somatic mutations validated by PCR and direct DNA Sanger sequencing on the same index HCL patient.

Immunohistological Analysis—Antibodies:

Primary antibodies used for immunohistological staining on paraffin sections are indicated below. Mouse monoclonal antibodies (MAb) directed against PAX5 (clone 24/PAX5) and Annexin A1 (clone 29) were obtained from BD Biosciences. Mouse monoclonal antibodies directed against CD20 (clone L26) and DBA44 were obtained from Dako, Glostrup, Denmark. Rabbit monoclonal antibodies against total ERK1/2 (clone 137F5, dilution: 1:250) or phospho-ERK1/2 (clone D13.14.4E, dilution 1:200) were both obtained from Cell Signaling (cat. #8201). Secondary Alexa fluorescinated 488 goat anti-mouse antibody and Alexa rhodaminated 568 goat anti-rabbit antibody were purchased from Molecular Probes, Eugene, Oreg.

Single Immuno-Enzymatic Staining in Paraffin Sections:
Paraffin sections from optimally formalin-fixed bone marrow trephines were subjected to antigen retrieval for 5 minutes at 85° C. (or 97° C. for the PAX5 staining) with Dako Target Retrieval Solution/High pH (Dako, cat. K8004) in Dako PT link (Dako, cat. PT101) and immunostained with the above primary antibodies. Antibody/antigen reaction was revealed using the Dako REAL LSAB+ kit detection system (Dako, cat. K5005). Sections were then counterstained in hematoxylin for 5 minutes.

As a control for the specificity of the phospho-ERK1/2 staining, sections were also stained in parallel with the anti-phospho-ERK1/2 antibody pre-incubated with its blocking phospho-peptide (Cell Signaling, cat. #1150).

Double Immuno-Enzymatic Staining in Paraffin Sections:
Paraffin sections from optimally formalin-fixed bone marrow trephines were subjected to antigen retrieval for 5 minutes at 85° C. (or 97° C. when the anti-PAX5 antibody was included) with Dako Target Retrieval Solution/High pH (Dako, cat. K8004) in Dako PT link (Dako, cat. PT101). Double immuno-enzymatic stainings with the anti-phosphoERK1/2 antibody and the mouse anti-PAX5 (1:50 dilution) or anti-CD20 antibodies (clone L26; 1:500 dilution) were performed using an immuno-peroxidase detection system (Dako LSAB+HRP, cat. K0690; Dako liquid DAB+Substrate and Chromogen, cat. K3468) for one antibody, followed by an immuno-alkaline phosphatase detection system (Dako REAL LSAB+, cat. K5005, with replacement of the red chromogen with a Fast Blue-based color development, Sigma, cat. F3378) for the other antibody. Sections were not counterstained.

As a control for the specificity of the phospho-ERK1/2 staining, sections were also stained in parallel with the anti-phospho-ERK1/2 antibody pre-incubated with its blocking phospho-peptide (Cell Signaling, cat. #1150).

Double Immunofluorescence Staining in Paraffin Sections:
Paraffin sections from optimally formalin-fixed bone marrow trephines were subjected to antigen retrieval for 5 minutes at 85° C. (or 97° C. when the anti-PAX5 antibody was included) with Dako Target Retrieval Solution/High pH (Dako, cat. K8004) in Dako PT link (Dako, cat. PT101). Sections were incubated for 1 hour with the rabbit monoclonal anti-phospho-ERK1/2 antibody (1:200 dilution) and the mouse monoclonal antibody antiPAX5 (1:25 dilution) or anti-CD20 (1:500 dilution). Following washing with Tris/EDTA buffer pH 7.6 for 5 minutes, the sections were incubated for 1 hour with a mixture of secondary Alexa fluorescinated 488 goat anti-mouse antibody and Alexa rhodaminated 568 goat anti-rabbit antibody (final dilution 1:100). Following washing in Tris/EDTA buffer pH 7.6, sections were allowed to dry at room temperature for 30 minutes and mounted in mowiol. As a control for the specificity of the phospho-ERK1/2 staining, sections were also stained in parallel with the anti-phospho-ERK1/2 antibody pre-incubated with its blocking phospho-peptide (Cell Signaling, cat. #1150).

Images were collected with a Zeiss LSM 510 confocal microscope (Carl Zeiss, Jena, Germany) using 488-nm (green fluorescence) and 543-nm (red fluorescence) laser lines for excitation. AOTF-controlled tuning of laser lines, pinhole diameters, and light collection configuration were optimized to obtain best signal-to-noise ratio and to avoid any fluorescence crossover. LSM 510 software (Carl Zeiss) was used for microscope regulation and collection of images. The images were transferred to a graphic work-station for further processing. Slices were reconstructed in 3D using the isosurface module of Imaris software (Bitplane, Zurich, Switzerland).

Western Blot Analysis:
Fresh leukemic cells purified from the peripheral blood of 5 patients with HCL were seeded in triplicate (2 to $3 \times 10^5$ cells/well, depending on the patient) in 96-well flat-bottom plates, and left recovering by overnight incubation at 37° C. and 5% CO2 in cell culture medium (RPMI1640 with 10% fetal bovine serum, glutamine and antibiotics). The day after, PLX4720 (Axon Medchem, cat. 1474), a specific inhibitor of active BRAF (Tsai et al., Proc Natl Acad Sci USA. 2008; 105:3041), was added at final concentrations of 250 nM, 500 nM or 1000 nM. DMSO (the drug vehicle) was added in parallel wells as control. Cells were then harvested at different time points (2 h, 6 h and 24 h), washed 3 times in PBS, lysed in Laemmli sample buffer and boiled at 95° C. for 5 minutes. In 2 of the 5 patients, frozen dry pellets of purified HCL cells were also lysed immediately after purification (without in vitro incubation). Protein lysates (6 to $7.5 \times 10^4$ fresh cell equivalent, depending on the patient; $2 \times 10^5$ frozen cell equivalent) were separated by SDS-polyacrylamide gel electrophoresis (SDS-PAGE) on pre-cast electrophoresis gels (12% Resolving gel cat. 456-1043 or Any kD Resolving Gel cat. 456-9036, Biorad), transferred to a 0.45 um pore size nitrocellulose transfer membrane (Whatman GmbH, Dassel, Germany), and probed with specific primary antibodies directly or after stripping (with Restore Western Blot Stripping Buffer, Pierce/Thermo Scientific cat. 21059). The anti-phospho-ERK1/2 (clone D13.14.4E; 1:2000 dilution), anti-phospho-MEK1/2 (clone 166F8; 1:1000 dilution), anti-ERK1/2 (clone 137F5; 1:1000 dilution) rabbit monoclonal antibodies and the anti-MEK1/2 (clone L38C12; 1:1000 dilution) mouse monoclonal antibody were all from Cell Signaling Technology. Upon incubation with horseradish peroxidase-conjugated secondary antibodies (GE Healthcare Lifesciences, Uppsala, Sweden), polypeptides were visualized using an enhanced chemiluminescence (ECL) western blot detection kit according to the manufacturer's instruction (GE Healthcare Lifesciences). Protein lysates ($3 \times 10^4$ to $2 \times 10^5$ cell equivalent, depending on the experiment) from either serum-starved (45 min at 37° C. and 5% $CO_2$ in RPMI1640) or unstarved human leukemic T-cell line Jurkat cells were used as negative and positive control, respectively, for ERK1/2 and MEK1/2 phosphorylation.

EXAMPLE 1

Case Report

A 47 year-old male presented with fever and pneumonia in March 2009. Laboratory data showed Hb 11.5 g/dL, WBC 6,100/mm³ (49% circulating leukemic hairy cells) and platelets 70,000/mm³. Splenomegaly was present. A bone marrow trephine showed a typical HCL histology. At immunohistochemistry, leukemic cells were positive for CD20, DBA44, CD68 and Annexin-A1; expression of CD20, CD11c, CD25 and CD103 was documented by flow cytometry. The patient was started on therapy with pentostatin (deoxycoformicin) and is now in complete hematological remission.

Identification of Candidate Somatic Mutations in a HCL Patient

Whole exome sequencing of genomic DNA from the patient's purified leukemic and non-leukemic cells produced ~42.5 and ~42.8 million reads, respectively, of 108 nucleotides length (Table S3). After removal of low quality and duplicate reads, the mean depth of the covered exome was 71 (tumor) and 70 (normal) (median 52 and 51, respectively), with 99% of the target exome being covered by at least one read, and 86% by at least 10 reads (Table S3).

TABLE S3

| Patient ID | Read Length | Number of Reads | | Depth | | Coverage % | |
|---|---|---|---|---|---|---|---|
| | | Total | Valid | Mean | Median | 1X | 10X |
| Tumor | 108 | 42509448 | 37020339 | 71 | 52 | 99 | 86 |
| Normal | 108 | 42815110 | 37199014 | 70 | 51 | 99 | 85 |

The SAVI algorithm identified 5 unique non-synonymous variants that were present specifically in the tumor DNA (27% to 49% of the reads), and identified the BRAF, CSMD3, SLC5A1, CNTN6, and OR8J1 genes (Tables S4 and S5).

TABLE S5

| Chr | Position (hg18 assembly) | Gene | R/V | AA change | N reads (Tumor) (F + R)/T | % | N reads (Normal) (F + R)/T | % | p-value Terr | Nerr | Germ |
|---|---|---|---|---|---|---|---|---|---|---|---|
| 11 | 55884461 | OR8J1 | C/T | L55F | (35 + 41)/154 | 49 | (0 + 0)/150 | 0 | 2E−85 | 1E+00 | 2E−85 |
| 3 | 1369124 | CNTN6 | T/G | L494R | (10 + 28)/93 | 41 | (1 + 0)/88 | 1 | 2E−39 | 8E−01 | 1E−32 |
| 8 | 113325883 | CSMD3 | G/A | P3440S | (14 + 14)/85 | 33 | (1 + 0)/105 | 1 | 2E−26 | 9E−01 | 4E−22 |
| 7 | 140099605 | BRAF | A/T | V600E | (9 + 18)/83 | 33 | (0 + 1)/81 | 1 | 2E−25 | 8E−01 | 3E−20 |
| 22 | 30807874 | SLC5A1 | A/C | I167L | (2 + 6)/30 | 27 | (0 + 0)/25 | 0 | 1E−07 | 1E+00 | 1E−07 |

R/V, reference/variant nucleotide as per hg18 assembly (note that the non-coding strand of BRAF is referred to here) AA, amino acid
N reads, number of variant reads (F, forward strand; R, reverse strand)
T, total number of reads covering the region
p-value, probability that the variant is due to a sequencing error in the tumor (Terr), a sequencing error in the normal (Nerr), and a germline mutation (Germ)

All 5 variants were validated as somatic in origin after targeted Sanger re-sequencing of paired tumor and normal DNA from the same patient (Tables S4 and S5). All mutations were heterozygous; they were presumably clonally represented in the tumor population (as also assessed by the comparable size of the corresponding peak in the chromatogram), and introduced amino acid substitutions in the encoded proteins (Table 1). The extremely low false discovery rate (near 0%) of the SAVI algorithm did not come at the expense of a low sensitivity. Indeed, sensitivity (proportion of true variants identified), as estimated from the number of known germline polymorphisms present in dbSNP130 and detected by the algorithm, was similar to other estimates of previous studies (Choi, et al. Proc Natl Acad Sci USA 2009; 106(45):19096-101; Ng, et al. PLoS Genet. 2008; 4(8):e1000160) (Table S6)

TABLE S6

|  | Tumor | Normal | Normal + Tumor (combined) | Normal + Tumor (common) |
|---|---|---|---|---|
| Total | 16105 | 15747 | 18083 | 13769 |
| Novel | 2720 | 2498 | 3787 | 1431 |
| Known | 13385 | 13249 | 14296 | 12338 |
| Non-synonymous | 7651 | 7458 | 8764 | 6345 |
| Synonymous | 8454 | 8289 | 9319 | 7424 |
| Heterozygous | 10712 | 10367 | 12384 | 8695 |
| Homozygous | 5393 | 5380 | 5794 | 4979 |

TABLE 1

Clinical and phenotypical features of the 47 HCL patients

| HCL Case | BRAF V600E | Sex | Age at first diagnosis | WBC at first diagnosis (/mm³) | Splenomegaly at first diagnosis | Immunophenotype of leukemic B cells[d] | | | | Previous therapy |
|---|---|---|---|---|---|---|---|---|---|---|
|  |  |  |  |  |  | ANXA1 | CD25 | CD11c | CD103 |  |
| 1[a] | yes | M | 62 | 2,470 | no | + | + | n.a. | + | IFN[h] |
| 2 | yes | M | 47 | 9,400 | yes | n.a. | + | + | + | none |
| 3 | yes | F | 41 | 3,760 | yes | + | n.a. | + | + | RTX[i] |
| 4 | yes | M | 62 | 6,710 | yes | + | + | + | + | none |
| 5 | yes | M | 56 | 6,240 | yes | n.a. | + | + | + | none |
| 6 | yes | F | 61 | 8,819 | yes | n.a. | + | + | + | none |
| 7 | yes | M | 39 | 2,980 | yes | + | n.a. | n.a. | n.a. | splenectomy, IFN, DCF[j], 2-CDA[k], RTX, 2-CDA |
| 8[b] | yes | M | 46 | 2,700 | yes | n.a. | + | + | + | none |
| 9 | yes | M | 60 | 5,470 | yes | + | + | + | + | DCF, 2-CDA, splenectomy |
| 10 | yes | M | 33 | 4,120 | yes | + | + | + | + | none |
| 11[a] | yes[c] | M | 46 | 11,390 | yes | n.a. | + | + | + | DCF, 2-CDA, splenectomy, IFN, FCR[l], CHOP[m], 2-CDA |
| 12 | yes | F | 68 | 5,300 | no | + | n.a. | n.a. | n.a. | none |
| 13 | yes | M | 70 | 9,350 | no | n.a. | + | + | + | none |
| 14 | yes | M | 48 | 2,100 | no | + | + | + | n.a. | none |
| 15 | yes | M | 75 | 3,720 | no | + | n.a. | + | n.a. | none |
| 16 | yes[c] | M | 39 | 4,800 | yes | + | + | + | + | DCF, 2-CDA, RTX, splenectomy |
| 17[a] | yes | M | 61 | 2,500 | yes | + | n.a. | n.a. | n.a. | none |
| 18[a] | yes | M | 63 | 1,300 | yes | + | n.a. | n.a. | n.a. | none |
| 19 | yes[c] | F | 60 | 7,800 | yes | n.a. | + | + | + | none |
| 20 | yes | F | 47 | 8,010 | yes | n.a. | + | + |  | none |
| 21 | yes | M | 55 | 2,330 | yes | n.a. | + | + | + | none |
| 22 | yes | M | 63 | 3,680 | yes | n.a. | + | + |  | none |
| 23 | yes | M | 33 | 9,900 | no | + | + | + | + | none |
| 24 | yes | F | 68 | 2,900 | yes | + | n.a. | + |  | none |
| 25 | yes | M | 59 | 4,880 | yes | + | n.a. | + | + | none |
| 26[a] | yes | F | 79 | 2,900 | yes | + | n.a. | n.a. | + | none |
| 27[a] | yes | M | 57 | 1,300 | yes | + | n.a. | n.a. | +[e] | none |
| 28[a] | yes | M | 72 | 2,000 | yes | + | n.a. | n.a. | +[f] | none |
| 29[a] | yes | M | 74 | 9,300 | yes | + | n.a. | n.a. | n.a. | splenectomy, IFN |
| 30[a] | yes | M | 71 | 7,400 | yes | + | n.a. | n.a. | n.a. | splenectomy, IFN |
| 31[a] | yes | M | 52 | 1,300 | yes | + | n.a. | n.a. | n.a. | none |
| 32 | yes | M | 66 | 51,000 | n.a. | n.a. | + | + | n.a. | none |

TABLE 1-continued

Clinical and phenotypical features of the 47 HCL patients

| HCL Case | BRAF V600E | Sex | Age at first diagnosis | WBC at first diagnosis (/mm³) | Splenomegaly at first diagnosis | Immunophenotype of leukemic B cells[d] | | | | Previous therapy |
|---|---|---|---|---|---|---|---|---|---|---|
| | | | | | | ANXA1 | CD25 | CD11c | CD103 | |
| 33 | yes | M | 52 | n.a. | n.a. | n.a. | + | + | n.a. | none |
| 34 | yes | M | 80 | 24,600 | n.a. | n.a. | + | + | n.a. | 2-CDA |
| 35 | yes | F | 77 | 34,700 | yes | n.a. | + | + | + | IFN |
| 36 | yes | M | 49 | 12,10 | n.a. | n.a. | + | + | + | none |
| 37 | yes | M | 51 | 37,900 | n.a. | n.a. | + | + | + | none |
| 38 | yes | M | 35 | 2 | yes | n.a. | + | + | + | none |
| 39 | yes | M | 45 | 7,800 | n.a. | n.a. | + | + | + | none |
| 40 | yes | F | 49 | 18,900 | n.a. | n.a. | + | + | + | none |
| 41 | yes | M | 44 | 2,610 | yes | n.a. | + | + | +[g] | IFN, DCF + IFN, 2-CDA, splenectomy |
| 42 | yes | M | 56 | 7,500 | yes | n.a. | + | + | + | none |
| 43 | yes | M | 48 | 14,110 | yes | n.a. | + | + | + | none |
| 44 | yes | M | 41 | 4,170 | yes | + | n.a. | n.a. | + | none |
| 45 | yes | F | 41 | 3,760 | no | + | n.a. | n.a. | + | RTX |
| 46 | yes | M | 56 | 36,070 | yes | n.a. | + | + | + | none |
| 47 | yes[c] | M | 67 | 39,000 | yes | n.a. | + | + | n.a. | CTX[n] |

[a]Previously studied by gene expression profiling (Ref. 5);
[b]Index patient subjected to whole exome sequencing;
[c]Present in a homozygous/hemizygous fashion;
[d]ANXA1 was assessed at immunohistochemistry whilst CD25, CD11c and CD103 were assessed at flow cytometry;
n.a. = not available;
[e]In 19% of HCL cells;
[f]In 22% of HCL cells;
[g]In 39% of HCL cells;
[h]Interferon;
[i]Rituximab;
[j]Deoxycoformycin;
[k]2-chloro-deoxyadenosine;
[l]Fludarabine, Cyclophosphamide, Rituximab;
[m]Cyclophosphamide, Adriamycin, Vincristine, Prednisone;
[n]Cyclophosphamide.

EXAMPLE 2

BRAF Mutations in HCL Samples

While little is known about the biological role of 4/5 affected genes (Table S7), BRAF represents the most frequently mutated gene encoding a protein kinase in human cancers (Davies, et al. Nature 2002; 417(6892):949-54). Thus, 46 additional HCL cases were screened for this mutation by PCR and direct DNA Sanger sequencing of BRAF exon15.

TABLE S7

| Gene ID | Gene Function | Reference |
|---|---|---|
| CNTN6 | Member of the immunoglobulin superfamily; glycosylphosphatidylinositol-anchored neuronal membrane protein that functions as a cell adhesion molecule | Walshi et al., Cell Biol Int Rep 1991 |
| CSMD3 | Poorly characterized protein, recently reported as mutated in the germline of patients with familial colorectal cancer | Gylfe et al, Int J Cancer 2010 |
| SLC5A1 | Member of the sodium-dependent glucose transporter family, which functions as the primary mediator of glucose and galactose uptake from the intestinal lumen | Martin et al, Nature Genetics 1996 |
| OR8J1 | G-protein-coupled olfactory receptor protein that is responsible for the recognition and transduction of odorant signals | Malnic et al, Proc Natl Acad Sci USA 2004 |

The features of these cases are shown in Table 1. Strikingly, a T->A transversion occurring at position 1860 of the BRAF mRNA RefSeq NM_004333.4 and resulting in a Val->Glu amino acid substitution at position 600 of the BRAF protein (V600E) was found in 46/46 HCL cases (47/47, including the index patient-100%). The mutation was somatic in origin, as it was absent in matched non-leukemic DNA of all 10 HCL cases investigated.

In 29/47 mutated HCL patients (including the index case), the high purity of leukemic cells (>90%) allowed analysis of the zygosity of the mutation without the interference of wild-type alleles contributed by contaminating non-leukemic cells. In 25/29 cases, the mutation appeared as a double peak (FIG. 2, top panels), strongly indicating a heterozygous lesion occurring in all cells of the leukemic clone. Specifically, Flow cytometry analysis of a HCL patient in FIG. 2, top panels, shows peripheral blood mononuclear cells partly with high forward and side scatter features (black events in the dot plot on the far left), expressing CD19 together with CD11c and CD103 (red events in the middle and right dot plot, respectively). Direct DNA Sanger sequencing of purified leukemic cells reveals a heterozygous T->A mutation (far right; arrow). In the remaining 4 patients, only the mutant peak was observed (FIG. 2, upper-middle panels), pointing to a homozygous/hemizygous clonal event. Specifically, FIG. 2, upper-middle panels, show another HCL case analyzed in paraffin sections from a bone marrow biopsy (×400). Diffuse marrow infiltration by HCL cells (far left; hematoxylin & eosin staining) that display positivity for CD20 (stain in the middle) and for ANXA1 (stain on the right). Purified HCL cells harbor a homozygous/hemizygous T->A mutation (far right; arrow).

In 17/47 HCL patients, the height of the mutated peak in the chromatogram relative to the proportion of leukemic cells in the analyzed samples (from 30% to 74%) was consistent with the mutation being clonal. In the remaining HCL case (patient 7 of Table 1), the fresh PB sample that was initially analyzed and found to be BRAF wild-type, turned out retrospectively to contain a proportion of leukemic cells far below the detection threshold of direct Sanger sequencing for a heterozygous clonal mutation (about 30% in our hands). Because this HCL patient is currently in remission with <0.1% leukemic cells circulating in the PB, the only sample with considerable leukemic infiltration that could be investigated from this case was an archival fixed-paraffin-embedded bone marrow biopsy. Although the quantity and quality of genomic DNA extracted from this sample were very poor, Sanger sequencing could be performed on the cloned faint PCR product, and 4/26 sequenced clones were mutated. In conclusion, the BRAF mutation was detected in all 47 HCL cases analyzed and was clonal in at least 46 of them.

EXAMPLE 3

BRAF Mutation in Other B-Cell Lymphomas/Leukemias

Given the high frequency of BRAF V600E in HCL, other peripheral B-cell lymphomas/leukemias were analyzed to determine whether the same variant was also present. Strikingly, none of the 193 cases investigated carried the mutation (Table S8).

TABLE S8

| Tumor Entity | Cases (n = 232) | | |
|---|---|---|---|
| | Analyzed | Mutated | % Mutated |
| Hairy Cell Leukemia | 47 | 47 | 100 |
| Splenic Marginal Zone Lymphoma | 21 | 0 | 0 |
| Splenic Lymphoma/Leukemia, Unclassifiable* | 15 | 0 | 0 |
| Chronic Lymphocytic Leukemia | 21 | 0 | 0 |
| Follicular Lymphoma | 35 | 0 | 0 |
| Diffuse Large B-cell Lymphoma | 71 | 0 | 0 |
| Mantle Cell Lymphoma | 18 | 0 | 0 |
| Burkitt Lymphoma | 12 | 0 | 0 |

*Includes HCL-variant and splenic red pulp small B-cell lymphoma according to the 2008 WHO classification.

Figure 2:
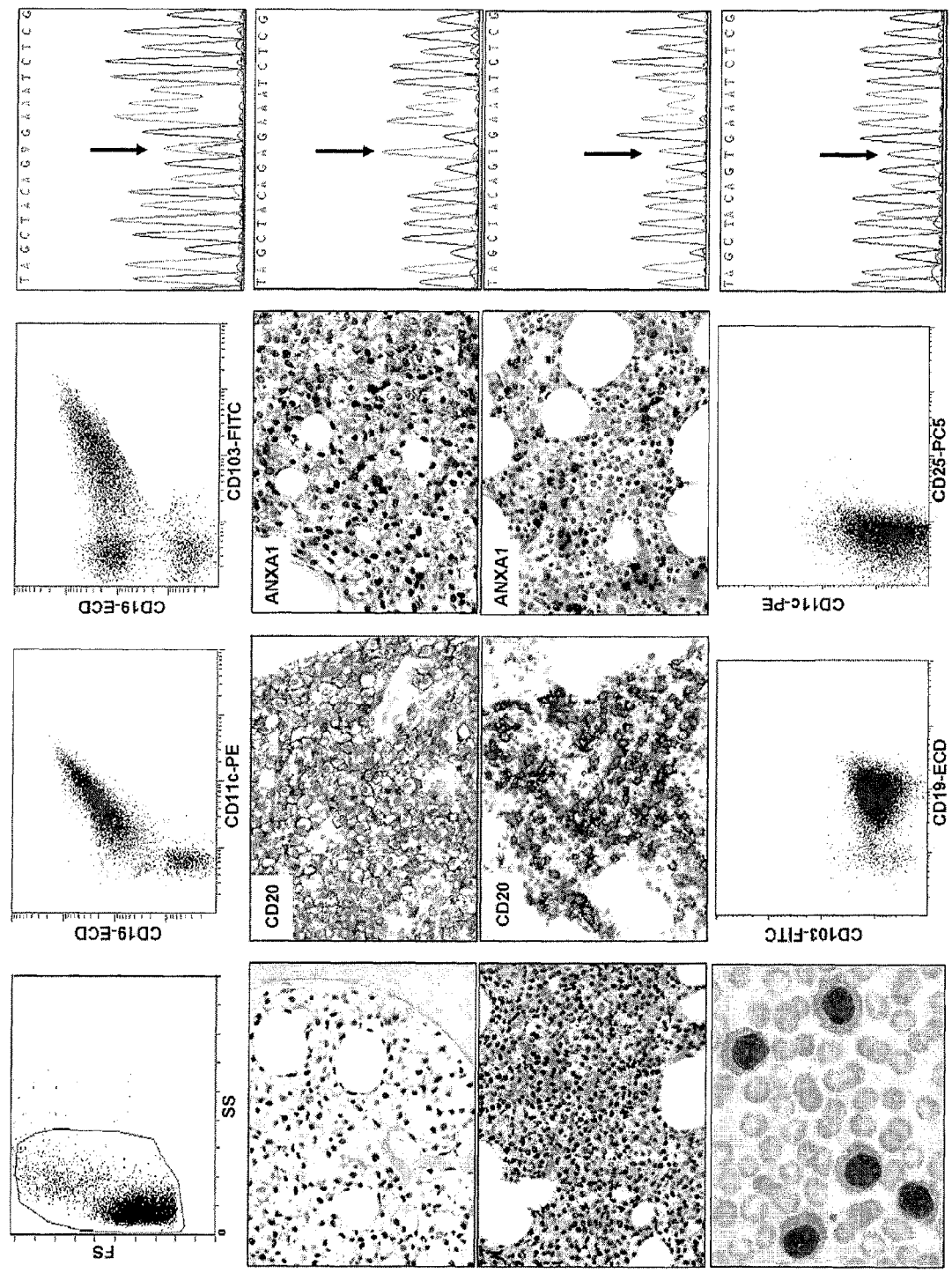
FIG. 2, top panels, show flow cytometry analysis of peripheral blood mononuclear cells from an HCL patient expressing CD19 together with CD11c and CD103. The far right panel shows direct sequencing of purified leukemic cells reveals a heterozygous T->A mutation (arrow).

BRAF-negative cases also included some B-cell tumors that, both clinically and morphologically, may simulate HCL (but have a different prognosis and clinical management), such as splenic marginal zone lymphoma (also frequently referred to as splenic lymphoma with villous lymphocytes) (n=21) and splenic B-cell lymphoma/leukemia, unclassifiable (n=15) (FIG. 2, lower-middle and bottom panels). Specifically, FIG. 2, lower-middle panel shows splenic Lymphoma/Leukemia Unclassifiable (paraffin sections from a bone marrow biopsy; ×400). Marked marrow infiltration by leukemic cells (far left; hematoxylin & eosin staining), that express CD20 (stain in the middle) but not ANXA1 (stain on the right, where positive myeloid cells act as internal control). Purified leukemic cells do not carry the T->A mutation (far right; arrow). FIG. 2, bottom panels, show splenic marginal zone lymphoma. Leukemic cells in the peripheral blood smear show the typical morphological features with polar villi (far left; May-Grünwald-Giemsa staining, ×630). At flow cytometry, leukemic cells express CD19 but not CD103 (red events in the left dot plot). These cells only weakly express CD11c and are negative for CD25 (red events in the right dot plot). Leukemic cells do not carry the T->A mutation (far right; arrow). The latter category includes HCL-variant and splenic red pulp small B-cell lymphoma, according to the 2008 WHO classification (Foucar, et al., WHO Classification of Tumours of Haematopoietic and Lymphoid Tissues. 4th ed. Lyon: International Agency for Research on Cancer (IARC); 2008:188-90).

EXAMPLE 4

Expression of Phosphorylated MEK and ERK in Leukemic Hairy Cells

The BRAF V600E mutation results in the constitutive activation of its kinase activity. Therefore, the phosphorylation status of MEK (the immediate downstream kinase target of BRAF) and ERK (the kinase phosphorylated by active MEK) was assessed using antibodies that specifically recognize phosphorylated MEK and ERK.

Figure 3:
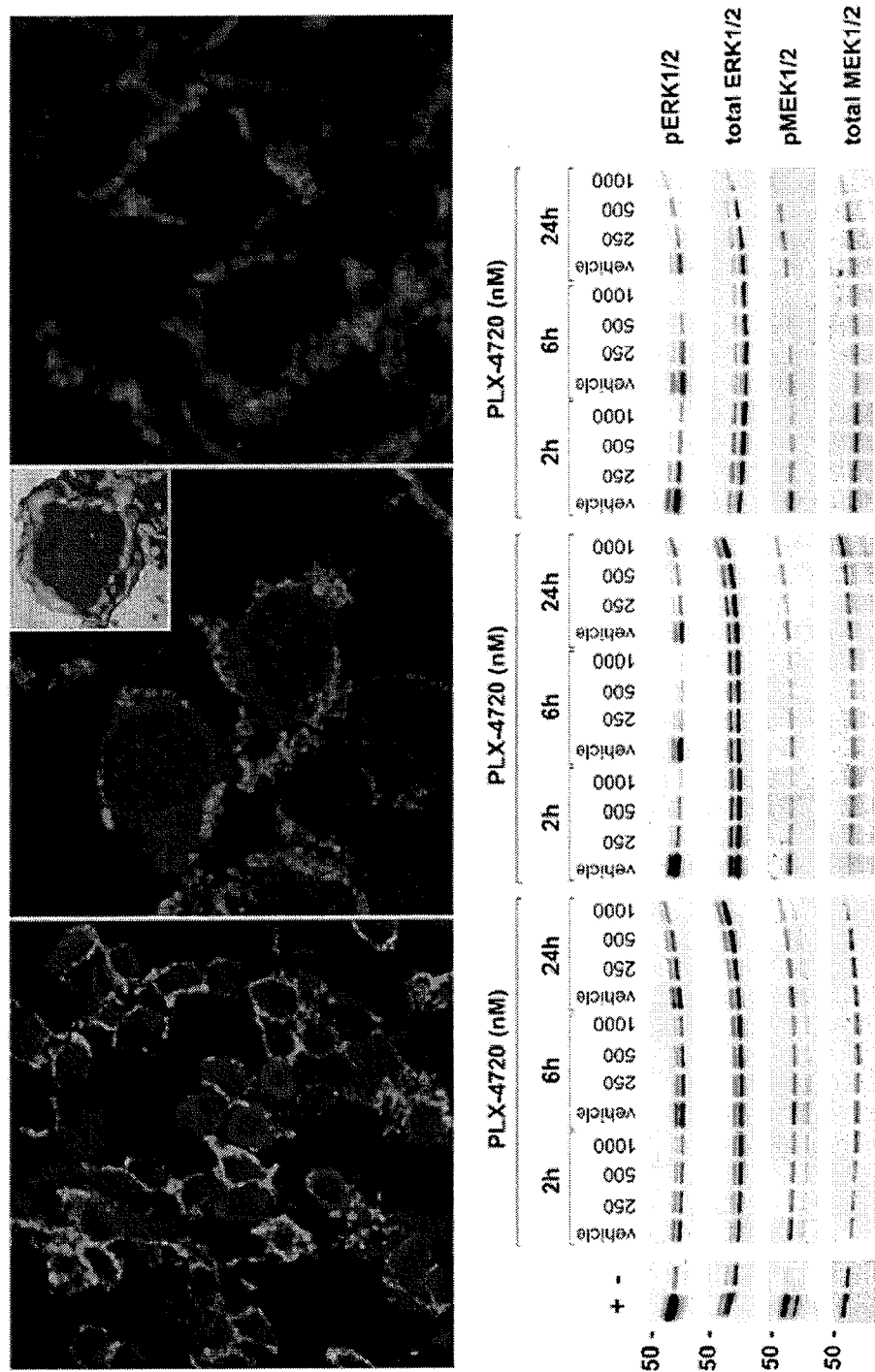
FIG. 3, top panels, are photographs showing double immunofluorescence staining for CD20 (green) and phospho-ERK (red) in paraffin sections from a bone marrow trephine infiltrated by HCL.

Because phospho-epitopes can be denatured by the decalcification process, immunohistological studies 5 BRAF-mutated HCL cases were selected for which optimally fixed/decalcified paraffin-embedded bone marrow biopsies were available. FIG. 3, top panels, show double immunofluorescence staining for CD20 (green) and phospho-ERK (red) in paraffin sections from a bone marrow trephine. The panels show the expression of phospho-ERK in CD20-positive leukemic hairy cells at lower (left) and higher magnification (middle). The inset shows a 3D reconstruction of confocal slices of a representative cell with the "isosurface" technique. The right panel shows that staining for phospho-ERK is completely blocked by pre-incubation of the antibody with the specific phospho-ERK peptide. FIG. 3, bottom panels, show Western blot analysis on purified HCL cells from 3 representative patients showing phosphorylation of both MEK and ERK kinases under basal conditions (vehicle treatment) and their dose-dependent dephosphorylation after 2, 6 and 24 h incubation with the specific active BRAF inhibitor PLX-4720 at 250 nM, 500 nM or 1000 nM concentrations. Membranes were probed with antibodies against phospho-ERK, phosphoMEK, total ERK and total MEK, as indicated on the far right. Protein lysates from either serum-starved or unstarved human leukemic Jurkat T cell line cells were used as negative (−) and positive (+) control, respectively, for ERK and MEK phosphorylation. Numbers on the left indicate molecular weight markers (in kDa).

Figure 4:
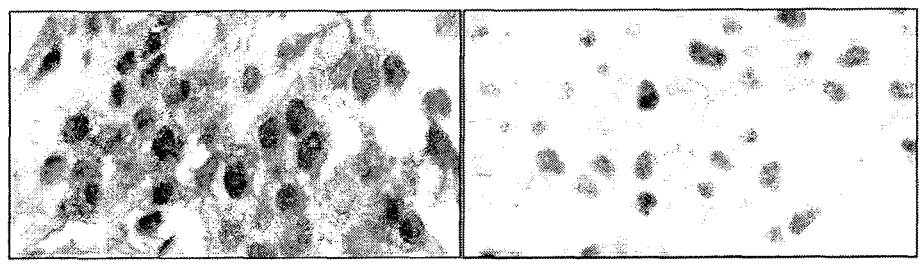
FIG. 4, left panel, shows leukemic hairy cells double stained for nuclear PAX5 (brown) and cytoplasmic phospho-ERK (blue).

In all cases, double immunohistochemical and/or immunofluorescence stainings for a B-cell marker (PAX5 or CD20) and phospho-ERK showed phosphorylated ERK in HCL cells, which was abolished by pre-incubation of the anti-phospho-ERK antibody with its blocking phosphopeptide (FIG. 3, top panels; FIG. 4). Phospho-MEK could not be investigated due to the unreliable staining of the anti-phospho-MEK antibody in paraffin sections. In 2/5 BRAF-mutated HCL patients that were phoso-ERK positive at immunohistochemistry a sufficient number of purified HCL cells was available for Western blot analysis. Both of them showed phosphorylation of MEK and its substrate ERK.

In vitro incubation of primary leukemic cells from 5 additional patients with the specific active BRAF inhibitor PLX-4720 led to marked decrease of phosphorylated MEK and ERK at low (≤1 μM) drug concentrations, while vehicle-treated cells retained MEK and ERK phosphorylation (FIG. 3, bottom panels).

We claim:

1. A method of monitoring minimal residual disease in a subject who has been treated for hairy cell leukemia with an anti-proliferative agent, the method comprising:
    obtaining a first urine sample from the subject, and
    detecting the BRAF V600E mutation, if present, in said sample,
    wherein said detecting comprises amplifying, by the polymerase chain reaction (PCR), a nucleic acid encoding said BRAF V600E mutation in said sample,
    wherein the detection of the BRAF V600E mutation indicates the presence of residual hairy cell leukemia in the subject and
    wherein the treatment with the anti-proliferative agent ended and no signs or symptoms of hairy cell leukemia was evident when the first urine sample was taken.

2. The method of claim 1, further comprising comparing the amount of said BRAF V600E mutation in said first urine sample with the amount of said BRAF V600E mutation determined in a urine sample from a subject not suffering from hairy cell leukemia or symptoms thereof.

3. The method of claim 1, further comprising sequencing said BRAF V600E mutation in the nucleic acids amplified by PCR.

4. The method of claim 1, further comprising administering a therapeutically effective amount of an anti-proliferative agent to said subject if the BRAF V600E mutation is in the sample.

5. The method of claim 4, wherein said anti-proliferative agent is a purine analog, and interferon, rituximab or bendamustine.

6. The method of claim 5, wherein said purine analog is pentostatin, cladaribine, azathioprine, mercaptopurine, thioguanine or fludarabine.

7. The method of claim 4, further comprising administering a therapeutically effective amount of a BRAF inhibitor.

8. The method of claim 7, wherein said BRAF inhibitor is PLX-4032 (Vemurafenib), GSK 2118436 (Dabrafenib), PLX-4720, SB590885, XL-281, RAF-265, GDC-0897, or Sorafenib.

9. The method of claim 4, further comprising administering a therapeutically effective amount of a MEK or ERK inhibitor.

10. The method of claim 9, wherein said MEK or ERK inhibitor is Any-142886/AZD-6244, SCIO-469, GW681323, U0126, XL-518, CI-1040, PD035901 or GSK1120212.

11. The method of claim 1, further comprising recommending the administration of a therapeutically effective amount of an anti-proliferative agent to said subject if the BRAF V600E mutation is present in the sample.

* * * * *

SEQUENCE LISTING

<160> NUMBER OF SEQ ID NOS: 14

<210> SEQ ID NO 1
<211> LENGTH: 2949
<212> TYPE: DNA
<213> ORGANISM: Homo sapiens

<400> SEQUENCE: 1

| | | | | | |
|---|---|---|---|---|---|
| cgcctcccctt | cccctcccc | gcccgacagc | ggccgctcgg | gccccggctc | tcggttataa | 60 |
| gatggcggcg | ctgagcggtg | gcggtggtgg | cggcgcggag | ccgggccagg | ctctgttcaa | 120 |
| cggggacatg | gagcccgagg | ccggcgccgg | cgccggcgcc | gcggcctctt | cggctgcgga | 180 |
| ccctgccatt | ccggaggagg | tgtggaatat | caaacaaatg | attaagttga | cacaggaaca | 240 |
| tatagaggcc | ctattggaca | aatttggtgg | ggagcataat | ccaccatcaa | tatatctgga | 300 |
| ggcctatgaa | gaatacacca | gcaagctaga | tgcactccaa | caaagagaac | aacagttatt | 360 |
| ggaatctctg | gggaacggaa | ctgattttc | tgtttctagc | tctgcatcaa | tggataccgt | 420 |
| tacatcttct | tcctcttcta | gcctttcagt | gctaccttca | tctctttcag | tttttcaaaa | 480 |
| tcccacagat | gtggcacgga | gcaaccccaa | gtcaccacaa | aaacctatcg | ttagagtctt | 540 |
| cctgcccaac | aaacagagga | cagtggtacc | tgcaaggtgt | ggagttacag | tccgagacag | 600 |
| tctaaagaaa | gcactgatga | tgagaggtct | aatcccagag | tgctgtgctg | tttacagaat | 660 |
| tcaggatgga | gagaagaaac | caattggttg | ggacactgat | atttcctggc | ttactggaga | 720 |
| agaattgcat | gtggaagtgt | tggagaatgt | tccacttaca | acacacaact | ttgtacgaaa | 780 |
| aacgttttc | accttagcat | tttgtgactt | ttgtcgaaag | ctgcttttcc | agggtttccg | 840 |
| ctgtcaaaca | tgtggttata | aatttcacca | gcgttgtagt | acagaagttc | cactgatgtg | 900 |
| tgttaattat | gaccaacttg | atttgctgtt | tgtctccaag | ttctttgaac | accaccaat | 960 |
| accacaggaa | gaggcgtcct | tagcagagac | tgccctaaca | tctggatcat | ccccttccgc | 1020 |
| acccgcctcg | gactctattg | ggccccaaat | tctcaccagt | ccgtctcctt | caaaatccat | 1080 |
| tccaattcca | cagcccttcc | gaccagcaga | tgaagatcat | cgaaatcaat | ttgggcaacg | 1140 |
| agaccgatcc | tcatcagctc | ccaatgtgca | tataaacaca | atagaacctg | tcaatattga | 1200 |
| tgacttgatt | agagaccaag | gatttcgtgg | tgatggagga | tcaaccacag | gtttgtctgc | 1260 |
| tacccccct | gcctcattac | ctggctcact | aactaacgtg | aaagccttac | agaaatctcc | 1320 |
| aggacctcag | cgagaaagga | agtcatcttc | atcctcagaa | gacaggaatc | gaatgaaaac | 1380 |
| acttggtaga | cgggactcga | gtgatgattg | ggagattcct | gatgggcaga | ttacagtggg | 1440 |
| acaaagaatt | ggatctggat | catttggaac | agtctacaag | ggaaagtggc | atggtgatgt | 1500 |
| ggcagtgaaa | atgttgaatg | tgacagcacc | tacacctcag | cagttacaag | ccttcaaaaa | 1560 |
| tgaagtagga | gtactcagga | aaacacgaca | tgtgaatatc | ctactcttca | tgggctattc | 1620 |
| cacaaagcca | caactggcta | ttgttaccca | gtggtgtgag | ggctccagct | tgtatcacca | 1680 |
| tctccatatc | attgagacca | aatttgagat | gatcaaactt | atagatattg | cacgacagac | 1740 |
| tgcacagggc | atggattact | tacacgccaa | gtcaatcatc | cacagagacc | tcaagagtaa | 1800 |
| taatatattt | cttcatgaag | acctcacagt | aaaaataggt | gattttggtc | tagctacagt | 1860 |
| gaaatctcga | tggagtgggt | cccatcagtt | tgaacagttg | tctggatcca | ttttgtggat | 1920 |
| ggcaccagaa | gtcatcagaa | tgcaagataa | aaatccatac | agctttcagt | cagatgtata | 1980 |
| tgcatttgga | attgttctgt | atgaattgat | gactggacag | ttaccttatt | caaacatcaa | 2040 |
| caacagggac | cagataattt | ttatggtggg | acgaggatac | ctgtctccag | atctcagtaa | 2100 |

-continued

```
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca aagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                            2949
```

<210> SEQ ID NO 2
<211> LENGTH: 766
<212> TYPE: PRT
<213> ORGANISM: Homo sapiens

<400> SEQUENCE: 2

```
Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
        50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
```

-continued

```
            210                 215                 220
Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
            290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
            370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
            450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
            530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640
```

```
Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tacctaaact cttcataatg cttgc                                    25

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gtaactcagc agcatctcag gg                                       22

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 5
tttgtgaata ctgggaacta tgaaa                                    25

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide sequence

<400> SEQUENCE: 6
tcatcctaac acatttcaag cc                                       22

<210> SEQ ID NO 7
<211> LENGTH: 25
<212> TYPE: DNA
<213> ORGANISM: Artificial Sequence
<220> FEATURE:
```

<223> OTHER INFORMATION: Oligonucleotide sequence

<400> SEQUENCE: 7
ttaatatgct ttgaaatcga caatg                                    25

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide sequence

<400> SEQUENCE: 8
caggtttgac accataacac aag                                      23

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 9
agccaacaaa tttcccttgt t                                        21

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 10
ccacaaatgg tggattagga a                                        21

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 11
aacctctctt ttcccccaaa                                          20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 12
agccacatag cggtcatagg                                          20

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 13
gttgtgtggc aaagaaactg c                                        21

```
<210> SEQ ID NO 14
<211> LENGTH: 23
<212> TYPE: DNA
<213> ORGANISM: Artificial Sequence
<220> FEATURE:
<223> OTHER INFORMATION: Oligonucleotide sequence

<400> SEQUENCE: 14
tcctcaagaa gagaaaccac ctc                                            23
```